(12) United States Patent
Malhotra et al.

(10) Patent No.: US 10,016,377 B2
(45) Date of Patent: Jul. 10, 2018

(54) TREATMENT OF HEPATITIS C USING HISTONE DEACETYLASE INHIBITORS

(71) Applicant: Cipla Limited, Mumbai (IN)

(72) Inventors: Geena Malhotra, Mumbai (IN); Kalpana Joshi, Maharashtra (IN)

(73) Assignee: Cipla Limited, Mumbia (IN)

( * ) Notice: Subject to any disclaimer, the term of this patent is extended or adjusted under 35 U.S.C. 154(b) by 0 days.

(21) Appl. No.: 15/684,192

(22) Filed: Aug. 23, 2017

(65) Prior Publication Data

US 2017/0348259 A1    Dec. 7, 2017

Related U.S. Application Data

(62) Division of application No. 15/370,275, filed on Dec. 6, 2016, now Pat. No. 9,763,901.

(30) Foreign Application Priority Data

Dec. 9, 2015   (IN) .......................... 4640/MUM/2015

(51) Int. Cl.
| | | |
|---|---|---|
| *A61K 31/185* | (2006.01) | |
| *A61K 9/20* | (2006.01) | |
| *A61K 45/06* | (2006.01) | |

(52) U.S. Cl.
CPC ............ *A61K 31/185* (2013.01); *A61K 9/205* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2059* (2013.01); *A61K 45/06* (2013.01)

(58) Field of Classification Search
CPC .................................................. A61K 31/185
USPC ........................................................ 514/625
See application file for complete search history.

(56) References Cited

U.S. PATENT DOCUMENTS

| | | |
|---|---|---|
| 9,763,901 B2 * | 9/2017 | Malhotra ............. A61K 31/185 |
| 2008/0161324 A1 | 7/2008 | Johansen et al. |
| 2011/0238003 A1 | 9/2011 | Bruno-Raimondi et al. |

FOREIGN PATENT DOCUMENTS

WO    2008033466 A2    3/2008

OTHER PUBLICATIONS

Wang, Chem.-Biol. Interactions, 34 (1981) 267-278.*
Bantscheff, et al., "Chemoproteomics profiling of HDAC inhibitors reveals selective targeting of HDAC complexes", Nature Biotechnology vol. 29 No. 3, 2011, 255-265.
Hillung, et al., "Characterization of the interaction between hepatitis C virus NS5B and the human oestrogen receptor alpha", Journal of General Virology 93, 2012, 780-785.
Murakami, et al., "Selective estrogen receptor modulators inhibit hepatitis C virus infection at multiple steps of the virus life cycle", Microbes and Infection 15, 2013, 45-55.
Watashi, et al., "Anti-hepatitis C Virus Activity of Tamoxifen Reveals the Functional Association of Estrogen Receptor with Viral RNA Polymerase NS5B", The Journal of Biological Chemistry vol. 282, No. 45, Nov. 9, 2007, 32765-32772.
Office Action issued in co-pending U.S. Appl. No. 15/364,825, dated Apr. 11, 2017.
Office Action issued in co-pending U.S. Appl. No. 15/364,825, dated Aug. 7, 2017.

* cited by examiner

*Primary Examiner* — Nizal S Chandrakumar
(74) *Attorney, Agent, or Firm* — Meunier Carlin & Curfman LLC

(57) ABSTRACT

The present invention relates to method of treatment of hepatitis C using bufexamac or a derivative thereof. The methods of the present invention can be used in patients with hepatitis C administering bufexamac or a derivative thereof in combination with one or more anti-hepatitis C drugs.

7 Claims, 1 Drawing Sheet

TREATMENT OF HEPATITIS C USING HISTONE DEACETYLASE INHIBITORS

CROSS REFERENCE TO RELATED APPLICATION

This application is a divisional of U.S. application Ser. No. 15/370,275, filed Dec. 6, 2016, and claims the benefit of Indian Application 4640/MUM/2015, filed Dec 9, 2015, the contents of each are incorporated by reference in their entirety.

FIELD OF THE INVENTION

The invention relates to methods of treating hepatitis C using histone deacetylase inhibitors, for instance bufexamac or derivative thereof, either alone or optionally in combination with one or more anti-hepatitis C drugs to a subject in need thereof. The invention also relates to compositions comprising bufexamac or a derivative thereof in an amount effective to treat hepatitis C, optionally in combination with one or more anti-hepatitis C drugs.

BACKGROUND

Hepatitis C is a largely asymptomatic liver disease caused by the hepatitis C virus (HCV). HCV is an escalating public health problem and burdens an estimated 3% of the world's population. According to the World Health Organization (WHO), approximately 130-150 million individuals worldwide have been infected with HCV, and about 5,00,000 deaths occur due to HCV-related liver diseases each year. The viral disease is transmitted sexually or parenterally by contaminated blood, blood products, and needles or from infected mothers or carrier mothers to their offspring. HCV infected patients, due to the high percentage of individuals inflicted with chronic infections are at an elevated risk of developing cirrhosis of the liver, subsequent hepatocellular carcinoma and terminal liver disease. HCV is the most prevalent cause of hepatocellular cancer and of patients requiring liver transplantations in the western world.

HCV has an RNA genome, as it is an envelope, positive-sense, single-stranded virus. At least six genetic strains of HCV have been identified and studied. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

The single strand HCV RNA genome is approximately 9,500 nucleotides in length and has a single open reading frame (ORF) encoding a single large polyprotein of about 3,000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV.

A number of potential molecular targets for drug development of direct-acting antivirals (DAAs) as anti-HCV therapeutics have now been identified including, but not limited to, the NS2-NS3 autoprotease, NS4A protease, the N3 protease, the N3 helicase, and the NS5B polymerase.

HCV infection is currently treated with antiviral medications, e.g. pegylated interferon (Peg-IFN) administered alone or in combination with ribavirin. Combination therapy with pegylated interferon (Peg-IFN) and ribavirin (RBV) is now successful in about half of the cases, but it is currently prohibitively expensive, requires long-term treatment, and is associated with suboptimal efficacy, poorer efficacy among patients with certain genotypes and common severe side-effects that make the treatment intolerable for many patients. In much of the world, such treatments are not economically feasible. New direct-acting antiviral drugs such as protease and polymerase inhibitors, either with or without interferon and/or ribavirin, have the potential to increase the response rate and to decrease the duration of treatment. Challenges facing current treatment of HCV include lack of efficacy in patients with difficult-to-treat disease, such as patients with cirrhosis or infected with HCV genotype 1 (who represent a majority of US HCV infections), the toxicity of combination therapy, and the difficulty of therapy, and the poor reception of these treatments by many patients.

Although attempts have been made in the prior art to develop new treatment options, new therapies for treating HCV-infected patients are desired which selectively inhibit HCV viral replication. It takes a great deal of time and money to develop a new drug from a novel chemical compound, hence, it may be easier to use previously developed drugs that can be used for new applications. Giving due consideration to the diversity of the drugs that are in existence, a way forward could be to determine the activity of the existing drugs to address the need for an alternative treatment for hepatitis C.

Histone deacetylases are a class of enzymes that remove acetyl groups from lysine residues in histone proteins. A variety of compounds are known to inhibit this process, and these compounds are collectively referred to as histone deacetylase (HDAC) inhibitors. These compounds were historically used as mood stabilizers and anti-epileptics, and more recently have been explored for other pathophysiologies including neurodegenerative diseases, cancer and herpes virus.

SUMMARY

According to one aspect of the invention, there is provided a method of treating hepatitis C comprising administering a histone deacetylase inhibitor.

According to one aspect of the invention, there is provided a method of treating hepatitis C comprising administering a non-steroidal anti-inflammatory histone deacetylase inhibitor.

According to another aspect of the invention, there is provided a method of alleviating or treating hepatitis C comprising administering bufexamac or a derivative thereof.

According to yet another aspect of the present invention, there is provided a method of alleviating or treating hepatitis C by administration of bufexamac or a derivative thereof in combination with one or more anti-hepatitis C drugs.

According to yet another aspect of the invention, there is provided a pharmaceutical composition comprising bufexamac or a derivative thereof for the treatment of hepatitis C.

According to another aspect of the present invention, there is provided a pharmaceutical composition comprising bufexamac or a derivative thereof in combination with one or more anti-hepatitis C drugs.

The details of one or more embodiments are set forth in the descriptions below. Other features, objects, and advantages will be apparent from the description and from the claims.

DETAILED DESCRIPTION

Figure 1:
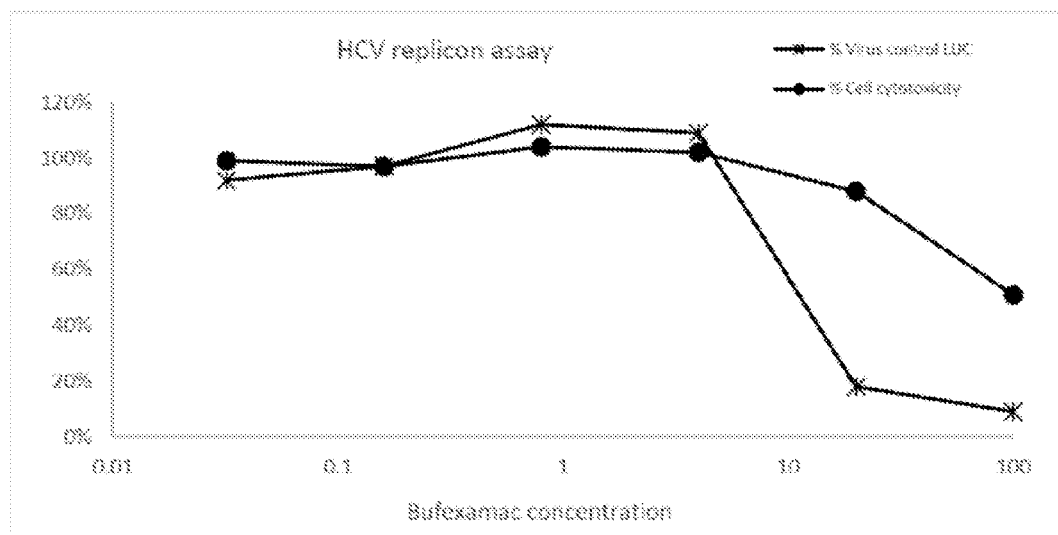
FIG. 1 includes a graph of Bufexamac in HCV GT1B Replicon assay.
Figure 2:
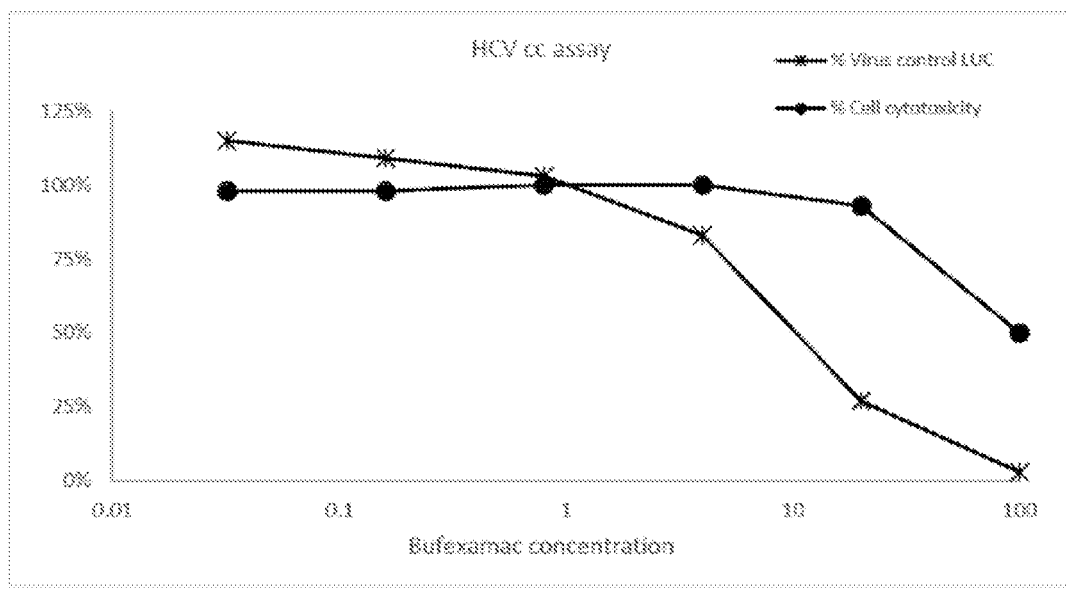
FIG. 2 includes a graph of graph for Bufexamac in HCVcc assay.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, or thiol, as described below.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, or thiol as described herein.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated, a substituent that is said to be "substituted" is meant that the substituent is substituted with one or more of the following: alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, or thiol. In a specific example, groups that are said to be substituted are substituted with a protic group, which is a group that can be protonated or deprotonated, depending on the pH.

Bufexamac is a non-steroidal anti-inflammatory aryl hydroxamic acid having the structure:

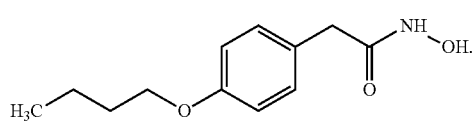 [SMILES: CCCCOc1ccc(CC(=O)NO)cc1]

Recent studies demonstrated that HDACs were also closely involved in HCV infection. Early research found that HCV-induced oxidative stress suppresses hepcidin expression through increased HDAC activity, and that the hepcidin plays a pivotal role as negative regulator of iron accumulation, which is characteristic of chronic hepatitis C. That is, the HCV infection can upregulate the activity of HDACs. Furthermore, polymorphisms in HDAC2, HDAC3 and HDAC5 have been found to be independently associated with sustained virologic response in chronic HCV. These observations suggested that HDAC inhibitors could hold promise in blocking HCV replication.

Disclosed herein are methods of treating hepatitis C in a patient in need thereof by administering to the patent an effective amount of bufexamac or derivative thereof. In some embodiments, a bufexamac derivative may be represented by a compound of Formula (1):

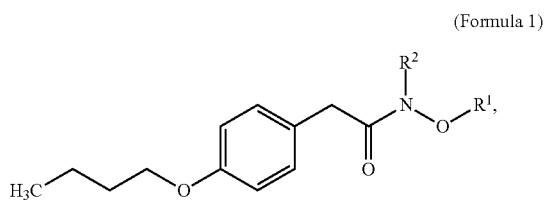

(Formula 1)

or a pharmaceutically acceptable salt thereof, wherein $R^1$ is selected from hydrogen, C(O)R, C(O)OR, C(O)NR$_2$R$_3$, and PO$_3$X$_2$;

$R^2$ is selected from hydrogen, C(O)R, C(O)OR, C(O)NR$_3$R$_4$, and PO$_3$X$_2$;

wherein R, $R^3$ and $R^4$ are in each case independently selected from hydrogen, optionally substituted C$_{1-8}$alkyl, optionally substituted C$_6$-C$_{12}$aryl, optionally substituted C$_{3-8}$cycloalkyl, optionally substituted C$_{2-12}$heterocyclyl, or optionally substituted C$_{2-12}$heteroaryl; and X is independently selected from hydrogen, pharmaceutically acceptable cation, or R (as defined above). In certain embodiments, it is preferred that at least one of $R^1$ and $R^2$ are hydrogen.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Preferably, bufexamac or derivative thereof may be administered to the subject once daily, twice daily or thrice daily. A typical recommended daily dosage regimen can range from about 20 mg to 2,000 mg, preferably from 10 mg to 1,000 mg, more preferably from 10 mg to 500 mg, more preferably from 10 mg to 100 mg. Preferably, bufexamac or derivative thereof may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution and sprinkles, transdermal patches, however, other dosage forms such as controlled release formulations, lyophilized formulations, modified release formulations, delayed release formulations, extended release formulations, pulsatile release formulations, dual release formulations and the like. Liquid and semisolid dosage forms (liquids, suspensions, solutions, dispersions, ointments, creams, emulsions, microemulsions, sprays, patches, spot-on), parenteral, topical, inhalation, buccal, nasal etc. may also be envisaged under the ambit of the invention. The inventors of the present invention have also found that the solubility properties of bufexamac may be improved by nanosizing thus leading to better bioavailability and dose reduction of the drug.

In one embodiment, bufexamac may be present in the form of nanoparticles which have an average particle size of less than 2,000 nm, less than 1,500 nm, less than 1,000 nm, less than 750 nm, less than 500 nm, or less than 250 nm.

Suitable excipients may be used for formulating the dosage form according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

Depending on the pathological stage, patient's age and other physiological parameters, and the extent of invasion, bufexamac or derivative thereof may require specific dosage amounts and specific frequency of administrations. Preferably, bufexamac or derivative thereof may be administered at least once, twice or thrice a day in an amount from 10 mg to 2,000 mg. In some embodiments, bufexamac or derivative thereof may be administered such that the total daily dose is in an amount from 10-1,000 mg, 50-1,000 mg, 50-750 mg, 50-500 mg, 100-500 mg, 250-2,000 mg, 500-2,000 mg, 500-1,000 mg, 250-1,000 mg, 250-500 mg, 1,000-2,000 mg, or 1,500-2,000. When bufexamac or derivative thereof is administered as a pharmaceutically acceptable salt, the dose levels refer the equivalent amount of bufexamac or derivative thereof free base.

In some embodiments, bufexamac or derivative thereof may be administered to a hepatitis C patient for a period of at least 2 weeks, at least 4 weeks, at least 6 weeks, at least 10 weeks, at least 12 weeks, at least 15 weeks, at least 20 weeks, at least 30 weeks, at least 40 weeks, or at least 52 weeks. In some instances, bufexamac or derivative thereof may be administered for a period of 2-52 weeks, 2-104 weeks, or 2-208 weeks.

Bufexamac or derivative thereof may be used for the treatment of hepatitis C in mammals, especially humans, in monotherapy mode or in a combination therapy (e.g., dual combination, triple combination etc.) mode such as, for example, in combination with one or more anti-hepatitis C drugs. In some instances, the bufexamac or derivative thereof or combination therapy can be administered to patients that are not undergoing estrogen replacement therapy, or in patients diagnosed with a condition for which estrogen replacement therapy is indicated.

There is provided a method of alleviating or treating hepatitis C by administration of bufexamac or derivative thereof optionally in combination with one or more anti-hepatitis C drugs.

Preferably, one or more anti-hepatitis C drugs that may be envisaged under the scope of the present invention may comprise from categories of anti-hepatitis C drugs for the treatment of hepatitis C such as, but not limited to, recombinant Human Interferon Alfa such as pegylated interferon alfa-2a or pegylated interferon alfa-2b (collectively "peginterferon" or "PEG"), nucleoside analogs for example ribavirin, direct acting antivirals (for example daclatasvir, boceprevir and telaprevir), NS3/4A protease inhibitors (PIs) (for example simeprevir), nucleotide NS5B polymerase inhibitors (for example sofosbuvir), NS5A Inhibitors (for example daclatasvir), non-nucleoside NS5B Polymerase Inhibitors (for example dasabuvir) or multi-class combination drugs (for example sofosbuvir/velpatasvir, ledipasvir/sofosbuvir, ombitasvir/paritaprevir/ritonavir, ombitasvir/paritaprevir/ritonavir and dasabuvir, elbasvir/grazoprevir, daclatasvir/asunaprevir/beclabuvir). Other possible additional agents include chlorcyclizine, hydroxyzine pamoate, benztropine mesylate, tamoxifen, clomifene, raloxifene, and muscarinic receptor antagonists (atropine, scopolamide, ipratropium, tiotropium, and the like).

The use of bufexamac or derivative thereof may preferably be associated with one or more of the above referenced anti-hepatitis C drugs as a combination therapy (either of the same functional class or other) depending on various factors like drug-drug compatibility, patient compliance and other such factors wherein the said combination therapy may be administered either simultaneously, sequentially, or separately for the treatment of hepatitis C.

Bufexamac or derivative thereof may be provided with one or more anti-hepatitis C drugs in the form of a kit, wherein the kit includes bufexamac or derivative thereof and at least one other anti-hepatitis C drug, and instructions for their administration to a hepatitis C patient.

According to the present invention there is provided a pharmaceutical composition comprising bufexamac or derivative thereof in combination with one or more anti-hepatitis C drugs.

In certain embodiments, the administration of bufexamac or derivative thereof, either alone or in combination with one or more anti-hepatitis drugs, can lower detectable HCV-RNA levels in a hepatitis patient. For instance, methods disclosed herein can lower HCV-RNA levels by at least 10%, at least 20%, at least 30%, at least 40%, at least 50%, at least 60%, at least 70%, at least 80%, at least 90%, or at least 95% relative to HCV-RNA levels prior to initiating treatment. In some instances, bufexamac or derivative thereof can be administered to a patient such no HCV-RNA is detectable in the patient after the treatment course is complete. HCV-RNA levels can be determined by quantitative, multi-cycle reverse transcriptase PCR. Such techniques are known, for instance in U.S. Pat. No. 6,172,046, col. 4, line 50-col. 6, line 5, which is hereby incorporated by reference. As used herein, no detectable HCV-RNA describes a condition in which there are less than 100 copies per ml serum of the patient.

The term "combination" as used herein, defines either a fixed combination in one dosage unit form, a non-fixed combination or a kit containing individual parts for combined administration.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a hepatitis C virus including viral resistance. Within the meaning of the present invention, the term "treat" also includes to arrest, delay the onset (i.e., the period prior to clinical manifestation of a disease) and/or reduce the risk of developing or worsening a disease.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

HCV Replicon Assay

Stable HCV replicons of different genotypes may be used for anti-HCV evaluation. We use the subgenomic HCV replicons of genotype 1a (H77 strain), 1b (Con1 strain), and 2a (JFH-1 strain), which are Huh7 human hepatoma cell lines that contains an HCV replicon.

The HCV replicon antiviral evaluation assay examines the effects of compounds at six serial dilutions. Human interferon alpha-2b (rIFNα-2b) and/or Sofosbuvir are included in each run as a positive control compound.

Briefly, the replicon cells are plated at 5,000 cells/well into 96-well plates that are dedicated for the analysis of cell numbers (cytotoxicity) or antiviral activity. On the following day, samples are diluted with assay media and added to the appropriate wells. Cells are processed 72 hours later when the cells are still sub-confluent. For the luciferase endpoint assay, HCV replicon levels are assessed as replicon-derived Luc activity. The concentration of drug that reduces cell viability is assessed by the fluorometric CytoTox-1 cell proliferation assay (Promega), (expressed as cell numbers). For the qRT-PCR/TaqMan assay, total RNA is extracted from the replicon cells using RNeasy 96 kit (Qiagen) according to the manufacturer's protocol. Real-time RTPCR/TaqMan assays are performed to measure copy numbers of the replicon RNA and cellular ribosomal RNA. Where applicable EC50 (concentration inhibiting HCV replicon by 50%), EC90 (concentration inhibiting HCV replicon by 90%), CC50 (concentration decreasing cell viability by 50%), CC90 (concentration decreasing cell viability by 90%) and SI (selectivity indices: CC50/EC50 and CC90/EC90) values are derived.

Infectious HCVcc Assay

Huh7.5 cells are grown in Dulbecco's modified essential media (DMEM), 10% fetal bovine serum (FBS), 1% penicillin-streptomycin (pen-strep), 1% Non-essential amino acids (NEAA) in a 5% CO2 incubator at 37° C. Huh7.5 cells are seeded at 1×104 cells per well into 96-well plates according to Southern Research Institute standard format. Test articles are serially diluted with DMEM plus 5% FBS. The diluted compound in the amount of 50 µl is mixed with equal volume of cell culture-derived HCV (HCVcc), then applied to appropriate wells in the plate. Human interferon alpha-2b (rIFNα-2b) and/or Sofosbuvir are included as a positive control. After 72 hr incubation at 37° C., the cells are lysed for measurement of luciferase activity using *Renilla* Luciferase Assay System (Promega) according to manufacturer's instruction. The number of cells in each well is determined by CytoTox-1 reagent (Promega). Test articles are tested at 6 serial dilutions in triplicate to derive, if applicable, EC50 and EC90 (concentration inhibiting HCVcc infectivity by 50% and 90%, respectively), CC50 (concentration decreasing cell viability by 50%) and SI (selectivity index: CC50/EC50) values (Table 1).

| Study | Study Title | Objective of study | CC50 | EC50 | Bufexamac (Selectivity index) |
|---|---|---|---|---|---|
| In vitro | In vitro HCV replicon assay | Check the efficacy of compounds post infection | >100 | 11.3 | >8.85 |
| In vitro | In vitro HCV cc assay | Check the efficacy of compounds pre infection | 100 | 10.2 | 9.80 |

Bufexamac showed significant anti-hepatitis C activity when tested in hepatitis C viral infectivity and HCV replicon assays as illustrated above.

Example 2

Dosage Forms

| Dosage form A - Bufexamac tablets | |
|---|---|
| Ingredients | Quantity/tablet (mg) |
| Bufexamac | 50-600 |
| Pre-gelatinised starch | 30-150 |
| Dextrin | 40-160 |
| Hypromellose | 30-60 |
| Croscarmellose sodium | 15-45 |
| Magnesium stearate | 5-20 |
| Hypromellose | 2.5-10 |
| Titanium dioxide | 3-10 |

| Dosage form A - Bufexamac tablets | |
|---|---|
| Ingredients | Quantity/tablet (mg) |
| Macrogol 400 | q.s |
| Purified water | q.s |

Manufacturing Process

Bufexamac, pre-gelatinised starch, dextrin, hypromellose and croscarmellose sodium sifted and blended. Sifted magnesium stearate was added to the blend of step 1 and the blend was lubricated. The lubricated blend was then compressed into tablets and coated

| Dosage form B - Bufexamac tablets | |
|---|---|
| Ingredients | Qty/tab (mg) |
| Bufexamac | 25-300 |
| Microcrystalline cellulose | 100-300 |
| Povidone | 4-16 |
| Corn Starch | 10-45 |
| Purified water | q.s. |
| Hypromellose (HPMC K4M/K15 M/K100 M) | 150-750 |
| Colloidal silicon dioxide | 1-6 |
| Talc | 3-12 |
| Magnesium Stearate | 3-12 |

Manufacturing Process

Bufaxamac, microcrystalline cellulose, and hypromellose were sifted and blended. Binder solution was prepared by dissolving povidone in purified water. The dry mix was granulated using the binder solution. Granules were then dried and were then blended with colloidal silicon dioxide and starch, followed by lubrication with magnesium stearate. The lubricated blend was then compressed into tablets.

| Dosage form C - Bufexamac tablets | |
|---|---|
| Ingredients | Quantity/tablet (mg) |
| Bufexamac | 10-400 |
| HPMC E 5 | 10-20 |
| Tri-calcium phosphate (TCP) | 30-150 |
| Mannitol | 40-160 |
| Microcrystalline cellulose | 30-60 |
| Croscarmellose sodium | 15-45 |
| Aerosil 200 pharma | 1-5 |
| Magnesium stearate | 5-20 |
| Purified water | q.s. |

Manufacturing Process

Bufaxamac, microcrystalline cellulose, TCP and mannitol were sifted and then dry mixed. Binder solution was prepared by dissolving HPMC in purified water. The binder solution was sprayed on dry mix. Granules were then dried and sized and were then blended with colloidal silicon dioxide, talc, followed by lubrication with magnesium stearate. The lubricated blend was then compressed into tablets.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A kit comprising an anti-hepatitis C effective amount of a compound of Formula I:

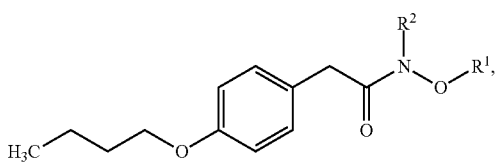

[Formula I]

or a pharmaceutically acceptable salt thereof, wherein
$R^1$ is selected from hydrogen, C(O)R, C(O)OR, C(O)NR$_2$R$_3$, and PO$_3$X$_2$;
$R^2$ is selected from hydrogen, C(O)R, C(O)OR, C(O)NR$_3$R$_4$, and PO$_3$X$_2$;
X is independently selected from hydrogen, pharmaceutically acceptable cation, or R;
wherein R, $R^3$ and $R^4$ are in each case independently selected from hydrogen, optionally substituted $C_{1-8}$alkyl, optionally substituted $C_6C_{12}$aryl, optionally substituted $C_{3-8}$cycloalkyl, optionally substituted $C_{2-12}$heterocyclyl, or optionally substituted $C_{2-12}$heteroaryl; and
at least one other anti-hepatitis C drug.

2. The kit of claim 1, wherein $R^1$ and $R^2$ are each hydrogen.

3. The kit of claim 1, wherein the one or more anti-hepatitis C drugs comprises recombinant Human Interferon Alfa (peginterferon), nucleoside analogs, direct acting antivirals, NS3/4A protease inhibitors, nucleotide NS5B polymerase inhibitors, NS5A inhibitors, non-nucleoside NS5B polymerase inhibitors, or a combination thereof.

4. The kit of claim 1, wherein the one or more anti-hepatitis drugs comprises pegylated interferon alfa-2a, pegylated interferon alfa-2b, ribavirin, daclatasvir, boceprevir, telapravir, simeprevir, sofosbuvir, daclatasvir, dasabuvir, ledipasivir, velpatasvir, paritaprevir, ombitasvir, elbasvir, grazoprevir, asunaprevir, beclabuvir, or a combination thereof.

5. The kit of claim 1, comprising a pharmaceutical composition comprising the compound of Formula I in an amount from 10-500 mg.

6. The kit of claim 5, wherein the composition comprising the compound of Formula I also comprises the at least one other anti-hepatitis C drug.

7. The kit of claim 1, comprising a first pharmaceutical composition comprising the compound of Formula I, and at least one other pharmaceutical composition comprising at least one other anti-hepatitis C drug.

* * * * *